United States Patent
Burns

(10) Patent No.: US 10,675,380 B2
(45) Date of Patent: Jun. 9, 2020

(54) NANO-TEXTURED BIOCOMPATIBLE ANTIBACTERIAL FILM

(71) Applicant: N2 Biomedical LLC, Bedford, MA (US)

(72) Inventor: Jason E. Burns, Cambridge, MA (US)

(73) Assignee: N2 BIOMEDICAL LLC, Bedford, MA (US)

( * ) Notice: Subject to any disclaimer, the term of this patent is extended or adjusted under 35 U.S.C. 154(b) by 113 days.

(21) Appl. No.: 15/366,021

(22) Filed: Dec. 1, 2016

(65) Prior Publication Data

US 2017/0157289 A1 Jun. 8, 2017

Related U.S. Application Data

(60) Provisional application No. 62/261,912, filed on Dec. 2, 2015.

(51) Int. Cl.

| | |
|---|---|
| *A61L 27/30* | (2006.01) |
| *A61L 27/54* | (2006.01) |
| *A61L 27/58* | (2006.01) |
| *A61L 31/16* | (2006.01) |
| *A61L 31/08* | (2006.01) |
| *A61L 31/14* | (2006.01) |
| *C23C 16/40* | (2006.01) |
| *C23C 14/14* | (2006.01) |
| *C23C 14/24* | (2006.01) |
| *C23C 16/56* | (2006.01) |
| *C23C 14/58* | (2006.01) |
| *A61K 6/58* | (2020.01) |

(52) U.S. Cl.
CPC .............. *A61L 27/306* (2013.01); *A61K 6/58* (2020.01); *A61L 27/54* (2013.01); *A61L 27/58* (2013.01); *A61L 31/088* (2013.01); *A61L 31/148* (2013.01); *A61L 31/16* (2013.01); *C23C 14/14* (2013.01); *C23C 14/24* (2013.01); *C23C 14/5833* (2013.01); *C23C 16/405* (2013.01); *C23C 16/56* (2013.01); *A61L 2300/404* (2013.01); *A61L 2300/606* (2013.01); *A61L 2400/12* (2013.01); *A61L 2400/18* (2013.01); *A61L 2420/02* (2013.01); *A61L 2420/06* (2013.01)

(58) Field of Classification Search
None
See application file for complete search history.

(56) References Cited

PUBLICATIONS

Ewald et al. "Antimicrobial titanium/silver PVD coatings on titanium", BioMedical Engineering OnLine, 5(22), 2006, pp. 1-10. (Year: 2006).*

Cui et al. "Biomaterials modification by ion-beam processing", Surface and Coatings Technology, 112, 1999, pp. 278-285. (Year: 1999).*

Manova et al. "Thin Film Deposition Using Energetic Ions", Materials, 3, 2010, pp. 4109-4141. (Year: 2010).*

Unosson et al. "Reactive combinatorial synthesis and characterization of a gradient Ag—Ti oxide thin film with antibacterial properties", Acta Biomaterialia, 11, 2015, pp. 503-510. (Year: 2015).*

Song et al., Surface Modification of Silicone Rubber by Ion Beam Assisted Deposition (IBAD) for Improved Biocompatibility, Journal of Applied Polymer Science, 96, 2005, pp. 1095-1101. (Year: 2005).*

Wang et al., "Structural Study of Titanium Oxide Films Synthesized by Ion Beam-Assisted Deposition", Scanning, 30, 2008, pp. 59-64. (Year: 2008).*

Jung et al., "Effects of Ion Beam—Assisted Deposition of Hydroxyapatite on the Osseointegration of Endosseous Implants in Rabbit Tibiae", The International Journal of Oral & Maxillofacial Implants, 16(6), 2001, pp. 809-818. (Year: 2001).*

Pogodin, Sergey et al., "Biophysical Model of Bacterial Cell Interactions . . . ", Biophysical Journal, vol. 104, Feb. 2013, pp. 835-840.

Lorenzetti, Martina et al., "The Influence of Surface Modification on Bacterial Adhesion", ACS Applied Material Interfaces, 2015, vol. 7, pp. 1644-1651.

Stolzoff, Michelle et al., "Decreased Bacterial Growth on Titanium Nanoscale Topographies . . . ", International Journal of Nanomedicine, Feb. 2017, pp. 1161-1169.

Nakajo, Kazuko et al., "Inhibitory Effect of Ti—Ag Alloy on Artificial Biofilm Formation", Dental Materials Journal, 2014, 33(3), pp. 389-393.

Hasan, Jafar et al., "Selective Bactericidal Activity of Nanopatterned Superhydrophobic Cicada . . . " Applied Microbiol Biotechnol, 2013, vol. 97, pp. 9257-9262.

Kelleher, Susan et al., "Cicada Wing Surface Topography . . . ", ACS Applied Materials and Interfaces, vol. 8(24), pp. 14966-14974.

Ewald, Andrea et al., "Antimicrobial Titanium/Silver PVD Coatings on Titanium", BioMedical Engineering Online, 2006, vol. 5:22, pp. 1-10.

(Continued)

*Primary Examiner* — Melissa L Fisher
(74) *Attorney, Agent, or Firm* — Hunter Clark PLLC

(57) ABSTRACT

Techniques and devices including a biocompatible antibacterial film are provided. An example method for depositing a biocompatible antibacterial film using physical vapor deposition (PVD) includes providing a substrate in a PVD processing chamber, forming a deposited film by co-depositing a first material and a second material onto the substrate from a vapor plume, wherein at least the first material is biocompatible and at least the second material is antibacterial, and nano-texturing the deposited film to produce nanoscale surface asperities that provide at least one of inhibition of bacterial growth, promotion of osseointegration, promotion of epithelial attachment, or promotion of endothelial attachment.

10 Claims, 10 Drawing Sheets

(56) References Cited

PUBLICATIONS

Tarquinio, Keiko et al., "Bactericidal Effects of Silver Plus Titanium Dioxide-Coated Endotracheal Tubes . . . ", Dove Press Journal, International Journal of Nanomedicine, 2010, vol. 5, pp. 177-183.
Mungkalasiri, Jitti et al., "CVD Elaboration of Nanostrutured TiO2—Ag Thin Films with Efficient Antibacterial Properties", DOI, vol. 16, pp. 35-41.

* cited by examiner

NANO-TEXTURED BIOCOMPATIBLE ANTIBACTERIAL FILM

CROSS-REFERENCE TO RELATED APPLICATIONS

This application claims the benefit of U.S. Provisional Application No. 62/261,912 filed Dec. 2, 2015, entitled "NANO-TEXTURED BIOCOMPATIBLE ANTIBACTERIAL FILM," the entire contents of which is hereby incorporated herein by reference.

STATEMENT REGARDING FEDERALLY SPONSORED RESEARCH

This invention is made with government support under grant number 1R43DE025526-01 awarded by the National Institute of Dental and Craniofacial Research. The government has certain rights in the invention.

BACKGROUND

Bio-implants often fail due to effects of bacterial diseases and/or insufficient integration of the medical device into the surrounding tissue. Typical medicinal and surgical treatment options are often inadequate with regard to preventing failure of these devices.

As one example, peri-implantitis is a disease characterized by progressive loss of bone surrounding dental implants which may occur years after successful implantation and normal osseointegration that promotes integration of the implant and surrounding bone tissue. The disease is initiated when bacteria carried by saliva colonize exposed surfaces of the implant forming a biofilm, which then initiates an inflammatory response in the host. When this initial infection spreads to affect the soft tissues immediately surrounding the implant the condition is referred to as peri-implant mucositis. Often the infection spreads further to affect the boney support around the implant. Bleeding or suppurating tissue surrounding an implant with concurrent bone loss is referred to as peri-implantitis. It is generally agreed that the bacteria responsible for peri-implantitis and peri-implant mucositis are drawn from the same population responsible for periodontal disease in natural teeth. In contrast, normal, well integrated implants are populated by the bacteria typical of healthy teeth. Peri-implantitis may affect patients many years after implant insertion.

As another example, periprosthetic infections can affect prosthetic limbs, for example, percutaneous osseointegrated prosthetic systems (PODS). PODS include prosthetic limbs attached via insertion of a portion of the prosthetic limb into the medullary canal of residual bone after a limb amputation. Periprosthetic infections may originate from the skin-implant interface. Additionally, an inadequate skin seal (e.g., lack of a stable epidermal protective later against bacteria), lack of epithelial-implant integration and subsequent downgrowth, sinus tract formation and immune responses to the presence of the implant can augment infection rates.

SUMMARY

The following summarizes some aspects of the present disclosure to provide a basic understanding of the discussed technology. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in summary form as a prelude to the more detailed description that is presented later.

Items and/or techniques described herein may provide one or more of the following capabilities, as well as other capabilities not mentioned. A biocompatible antibacterial film is deposited using a physical vapor deposition (PVD) process. One or more constituent materials of the antibacterial film may inhibit bacterial growth on the surface of the film. Nano-scale asperities produced by the PVD process may inhibit bacterial growth on the surface of the film and/or promote at least one of osseointegration, epithelial attachment, or endothelial attachment. PVD processing parameters may be adjusted to produce nano-scale asperities of a particular dimension. The particular dimension may correspond to a surface roughness that inhibits growth of a particular pathogenic bacteria in the biological environment of the implant and/or promotes at least one of osseointegration, epithelial attachment, or endothelial attachment. Silver incorporated into a ceramic matrix may provide antibacterial effects with a slow elution rate. The slow elution rate along with the nano-scale asperities and the ceramic matrix may provide antibacterial properties over long time periods (e.g., weeks, months, years). Such a film provides two modes of bacterial inhibition, with a first mode provided by the anti-bacterial properties of the constituent materials of the deposited film and a second mode provided by the surface morphology of the deposited film. In this way, the deposited film may provide a bio-implant with substantially improved longevity with regard to antibacterial efficacy as compared to films providing only one or none of these modes. Other capabilities may be provided and not every implementation according to the disclosure must provide any, let alone all, of the capabilities discussed. Further, it may be possible for an effect noted above to be achieved by means other than that noted and a noted item/technique may not necessarily yield the noted effect.

An example of a method of depositing a biocompatible antibacterial film using physical vapor deposition (PVD) according to the disclosure includes providing a substrate in a PVD processing chamber, forming a deposited film by co-depositing a first material and a second material onto the substrate from a vapor plume, wherein at least the first material is biocompatible and at least the second material is antibacterial, and nano-texturing the deposited film to produce nano-scale surface asperities that provide at least one of inhibition of bacterial growth, promotion of osseointegration, promotion of epithelial attachment, or promotion of endothelial attachment.

Implementations of such a method may include one or more of the following features. The method may include nano-texturing the deposited film by sputtering with an ion beam having an energy of 50 eV-3000 eV. The method may include forming the deposited film and nano-texturing the deposited film in the presence of an ion:evaporant atom arrival ration, R, of $0.02 \leq R \leq 1$. The method may include forming an adhesion layer between the substrate and the deposited film. The method may include forming the adhesion layer by depositing the first material from the vapor plume onto the substrate prior to the co-depositing and gradually adding the second material to the vapor plume. The method may include backfilling the processing chamber with a reactive gas and forming the deposited film in the presence of the reactive gas such that the deposited film includes a ceramic component, the ceramic component being composed of the first material and an element of the reactive gas. The method may include selecting a ratio of the first material and the second material and forming the deposited film by co-depositing the first material and the second material using the selected ratio. The substrate may include one or more of a dental implant, a percutaneous device, an osseointegrated device, a percutaneous osseointegrated prosthesis, an orthopedic joint replacement, an orthopedic fixation pin, an orthopedic fixation plate, a percutaneous cochlear implant, a spinal disk replacement device, or a vascular device.

An example of biocompatible antibacterial film according to the disclosure includes at least a first material and a second material, wherein at least the first material is biocompatible and at least the second material is antibacterial and a nano-textured surface including nano-scale surface asperities that provide at least one of inhibition of bacterial growth, promotion of osseointegration, promotion of epithelial attachment, or endothelial attachment.

Implementations of such a biocompatible antibacterial film may include one or more of the following features. The first material may be a ceramic. The first material may be titania. The first material may be titanium and the second material may be silver. The biocompatible antibacterial film may include a third material and the first material may be titanium, the second material may be silver, and the third material may be titania. The second material may be silver. In an embodiment, an elution rate for the silver may be between 0.1 $\mu g/cm^2$/year and 100 $\mu g/cm^2$/year. In another embodiment, the elution rate for the silver may be between 0.5 $\mu g/cm^2$/year and 10 $\mu g/cm^2$/year. The nano-textured surface may have a root mean square roughness of greater than or equal to 5 nm and may include nano-scale surface asperities of a dimension between 10 and 1000 nanometers known to provide at least one of inhibition of growth of pathogenic bacteria, promotion of osseointegration, or promotion of epithelial attachment.

An example of a bio-implant according to the disclosure includes an implant device and a surface coating on the implant device including at least a first material and a second material, wherein at least the first material is biocompatible and at least the second material is antibacterial and a nano-textured surface including nano-scale surface asperities that provide at least one of inhibition of bacterial growth, promotion of osseointegration, promotion of epithelial attachment, or promotion of endothelial attachment.

Implementations of such a bio-implant may include the following feature. The implant device may include a dental implant, a percutaneous device, an osseointegrated device, a percutaneous osseointegrated prosthesis, an orthopedic joint replacement, an orthopedic fixation pin, an orthopedic fixation plate, a percutaneous cochlear implant, a spinal disk replacement device, or a vascular device.

Other aspects, features, and embodiments of the present invention will become apparent to those of ordinary skill in the art, upon reviewing the following description of specific, exemplary embodiments of the present invention in conjunction with the accompanying figures. While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with the various embodiments of the invention discussed herein. In similar fashion, while exemplary embodiments may be discussed below as device, system, or method embodiments it should be understood that such exemplary embodiments can be implemented in various devices, systems, and methods.

BRIEF DESCRIPTIONS OF THE DRAWINGS

Figure 4:
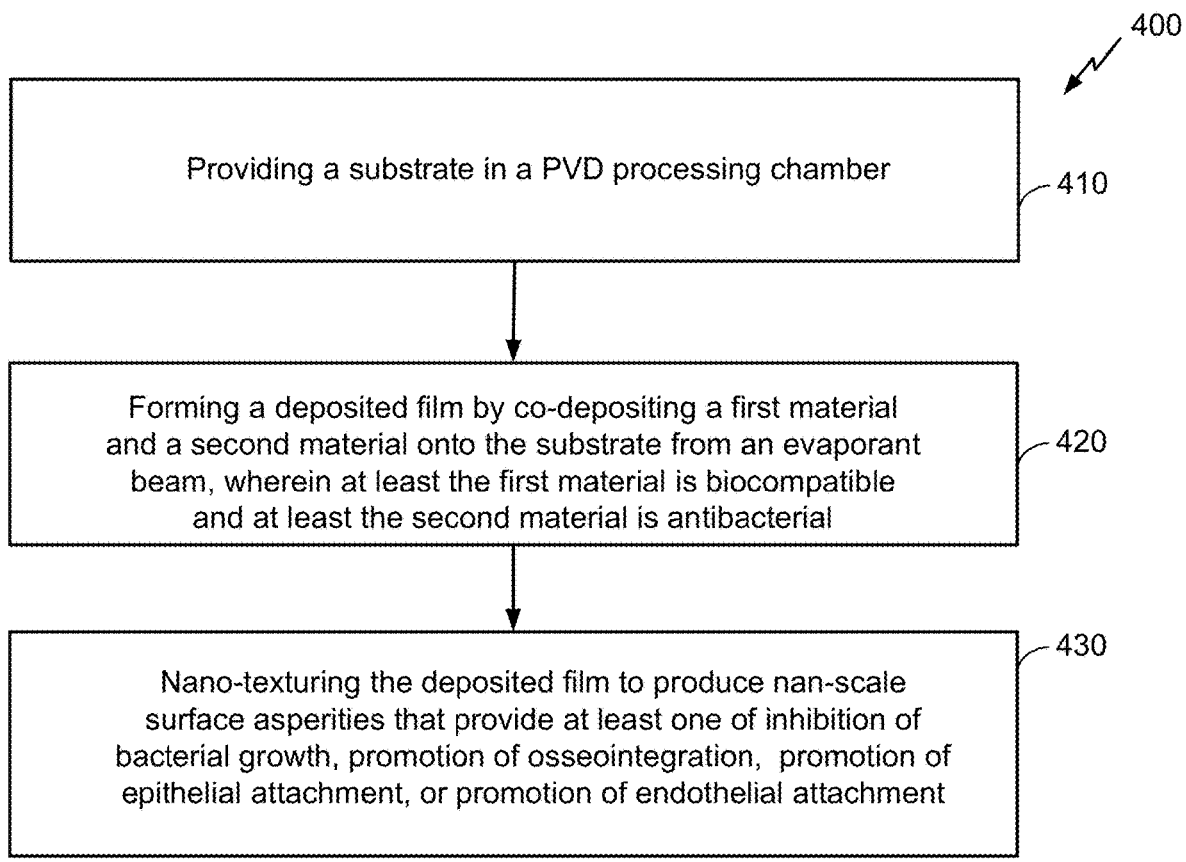
FIG. 4 is a block diagram of a method of growing a biocompatible antibacterial film using PVD.
Figure 5A:
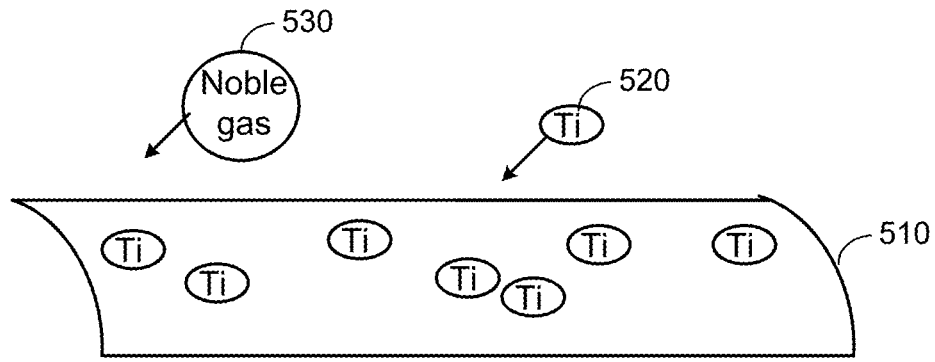
Figure 5B:
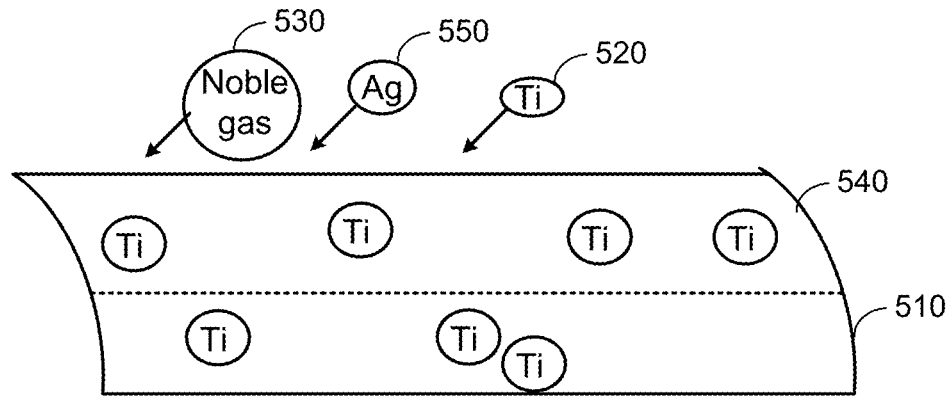
Figure 5C:
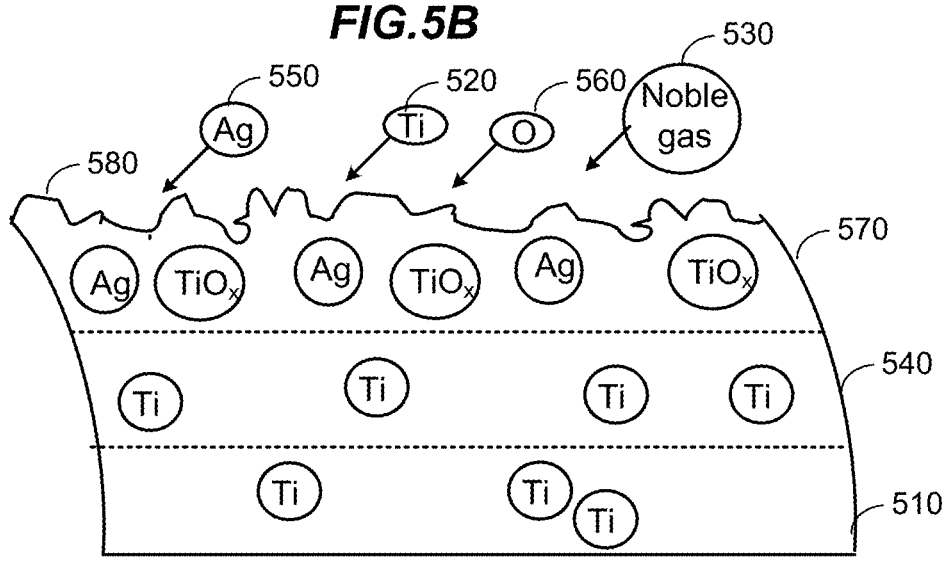

FIGS. 5A, 5B, and 5C are schematic diagrams of the biocompatible antibacterial film at various stages of the method in FIG. 4.

Figure 6:
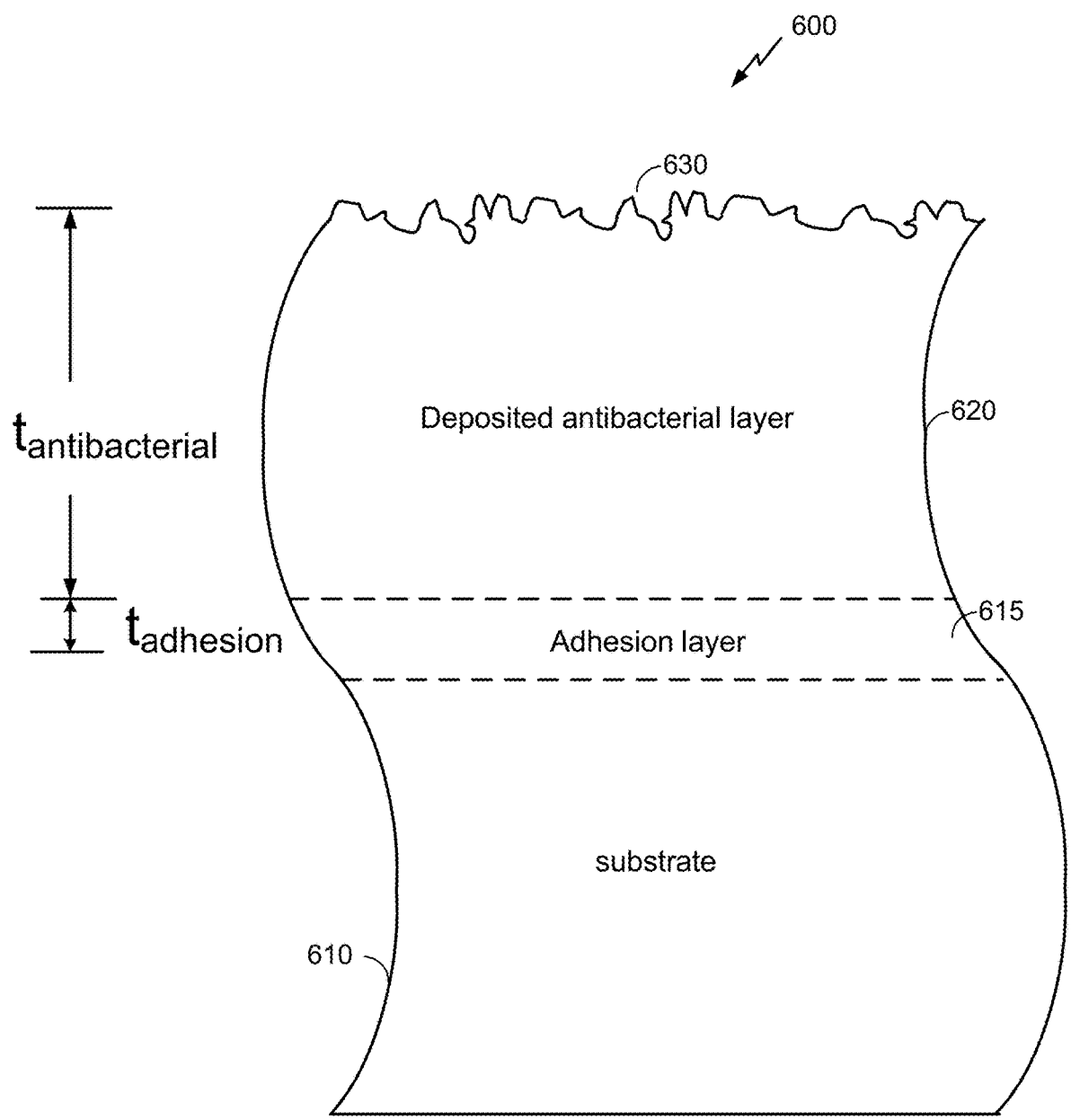

FIG. 6 is a schematic diagram of an example of a titania/silver antibacterial biocompatible film deposited on a titanium substrate.

Figure 7:
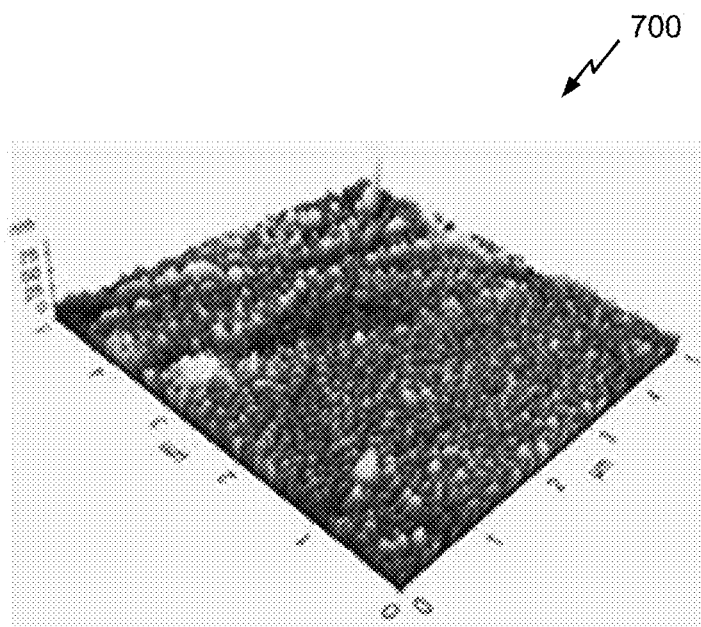

FIG. 7 is an example of an atomic force microscopy (AFM) scan of the film in FIG. 6.

Figure 8:
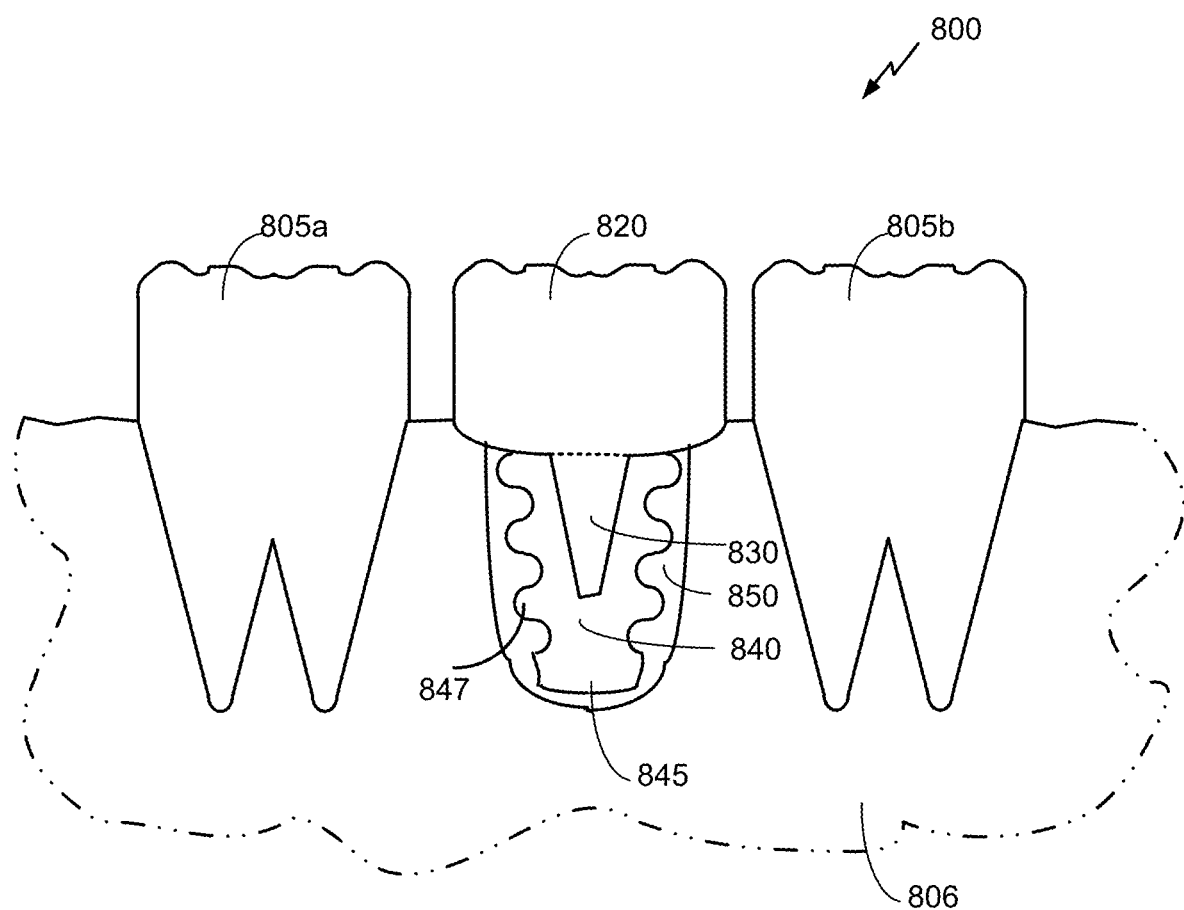

FIG. 8 is a schematic diagram of a dental implant system.

Figure 9:
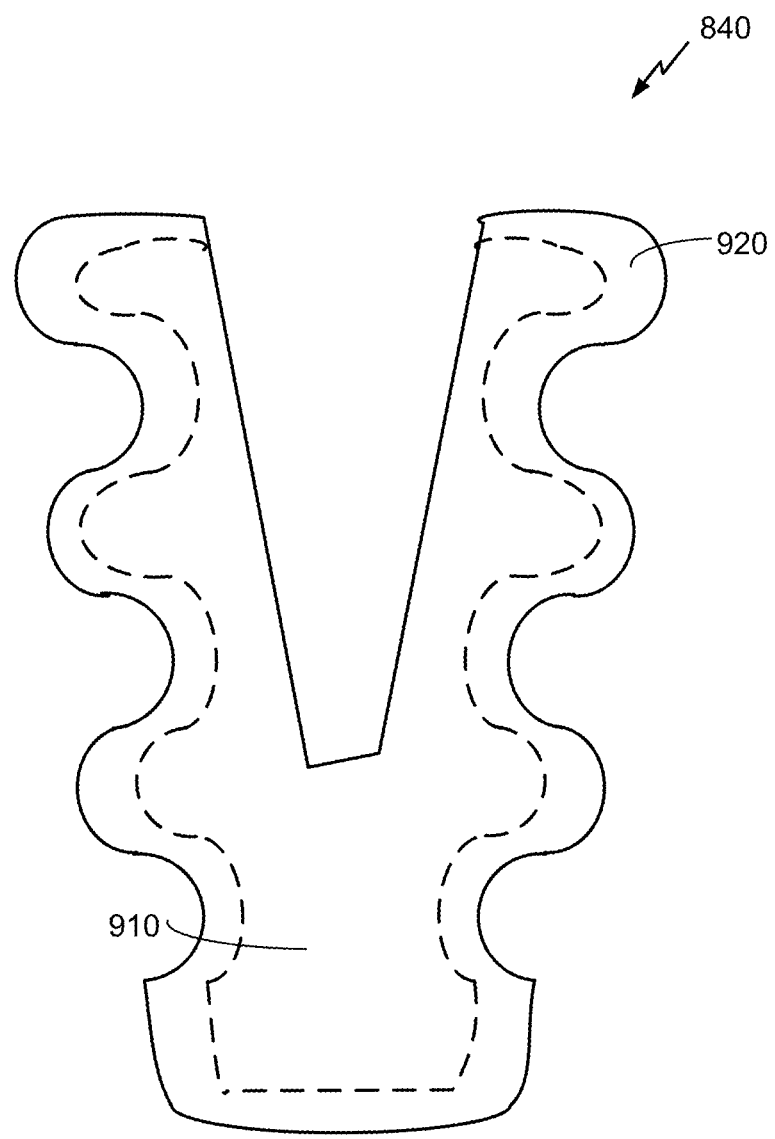

FIG. 9 is a schematic diagram of a dental implant that includes a biocompatible antibacterial film.

Figure 10:
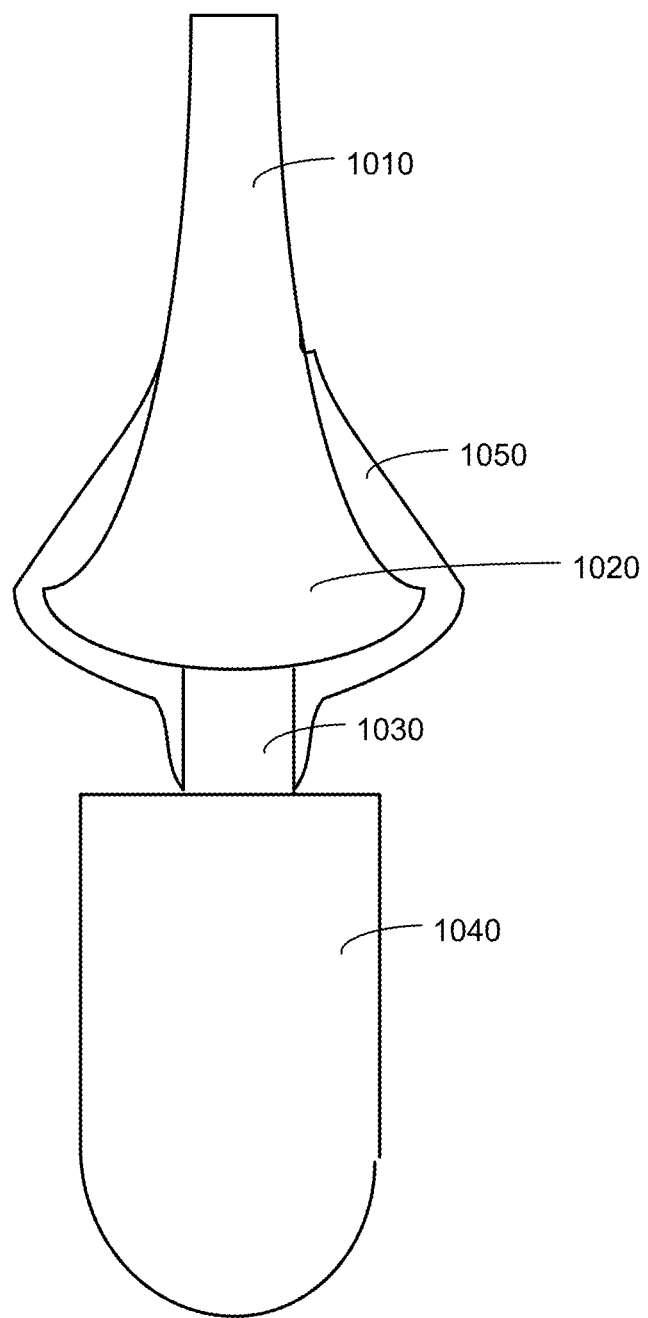

FIG. 10 is a schematic diagram of a percutaneous osseointegrated system that includes a biocompatible antibacterial film.

DETAILED DESCRIPTION

Techniques are provided for growing and using a biocompatible antibacterial film. The techniques discussed below are exemplary, however, and not limiting of the invention as other implementations in accordance with the disclosure are possible.

A biocompatible antibacterial film is deposited using a physical vapor deposition system. The antibacterial film is deposited on a substrate which may be a bio-implant. At least a portion of the bio-implant may be substantially composed of titanium. A first portion of the deposited film may be an adhesion layer. The adhesion layer may be a homo-metallic layer corresponding to an intermixed zone including substrate elements and deposited elements. The deposited antibacterial film may include a ceramic matrix doped with an antibacterial metallic component. The ceramic matrix may be titania ($TiO_x$) and the metallic component may be silver (Ag). A surface of the deposited film may include nano-scale asperities. Processing parameters of the deposition process may be adjusted to control the composition and morphology of the deposited film and to produce nano-scale asperities of particular dimensions. The particular dimensions may inhibit growth of particular pathogenic bacteria in the biological environment of the implant and/or may promote attachment and proliferation of cells corresponding to the implant environment (e.g., osseointegration, epithelial attachment, etc.). Further, the metallic component of the deposited film may provide active antibacterial properties. The deposited film may exhibit a slow elution rate of the antibacterial metallic component.

Surface modification of bio-implants may control bacterial growth while also encouraging osseointegration, epithelial attachment and/or endothelial attachment. Evaluation parameters for a surface modification technique and/or a surface produced by the surface modification technique include, but are not limited to, rate of osseointegration, epithelial attachment, and/or endothelial attachment, degree of osseointegration, epithelial attachment and/or endothelial attachment, reduction of pathogenic bacterial growth, longevity, and long-term biocompatibility. An effective surface treatment results in a surface that exhibits a high rate of osseointegration, epithelial attachment, and/or endothelial attachment and targeted reduction of pathogenic bacterial growth.

Antibiotic drugs may be deposited directly on the surface of implants, or incorporated as a component of an applied surface film (e.g., a biodegradable polymer film may include antibiotics). The surface film may decompose during use and release the antibiotic drugs as it decomposes. Such an approach may be effective for a relatively short active period (e.g., over a period of weeks or months) for resolving infections from the surgical procedure. However, the effectiveness of such a decomposing surface film may be limited with regard to longevity and long-term biocompatibility (e.g., over a period of months or years). Further, antibacterial drugs may not discriminate between pathogenic bacteria and non-pathogenic bacteria.

As an example of surface modification that may provide improved anti-bacterial properties at least for example as compared to treating a surface with antibiotic drugs, a nano-textured film may be deposited on the surface of the bio-implant. The nano-textured film deposited on the bio-implant surface may provide and/or promote active antibacterial properties. The surface energy associated with nano-scale surface features (i.e., features characterized by dimensions less than 100 nm), as opposed to larger features, may allow the dimensions of these features to be tailored to specific biological applications and functions. Mathematical models may predict the nanometer surface feature size in the deposited film that may alter surface energy to control specific cell responses. Surface energy affects how ions, proteins, and other bioactive agents adsorb to surfaces which in turn will alter cell adhesion, growth, genetic profile, etc. For example, protein adsorption may decrease bacteria functions, inhibit inflammation (e.g., via reduced macrophage functions), reduce infection, increase endothelialization, and/or increase bone growth. Surface roughness may increase surface wettability to promote fibronectin adsorption. In this way, the nano-scale surface features may decrease bacteria growth and increase bone and/or skin growth without usage of medications or drugs.

Figure 1:
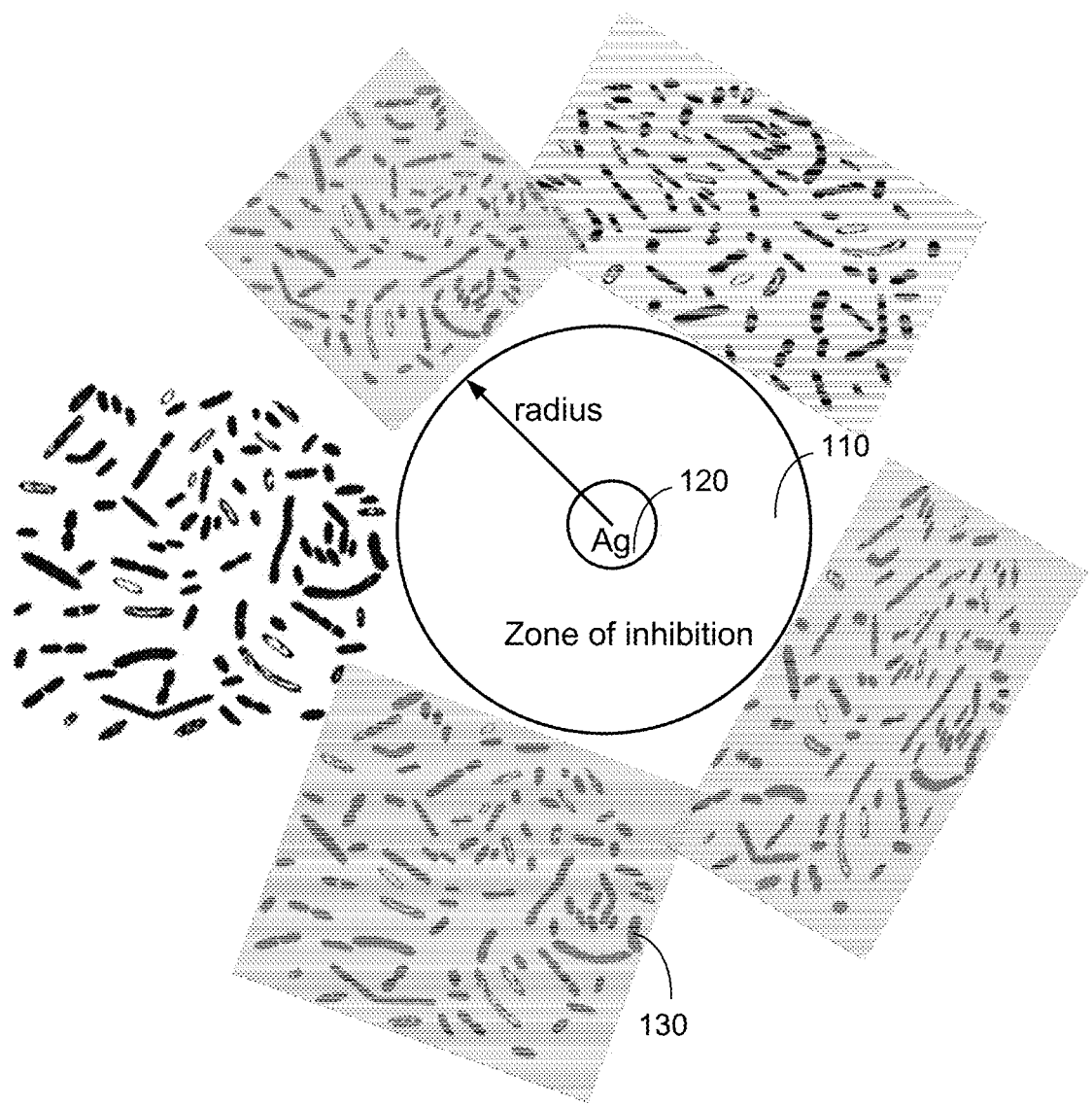
FIG. 1 is a schematic diagram of a zone of inhibition.
Figure 2A:
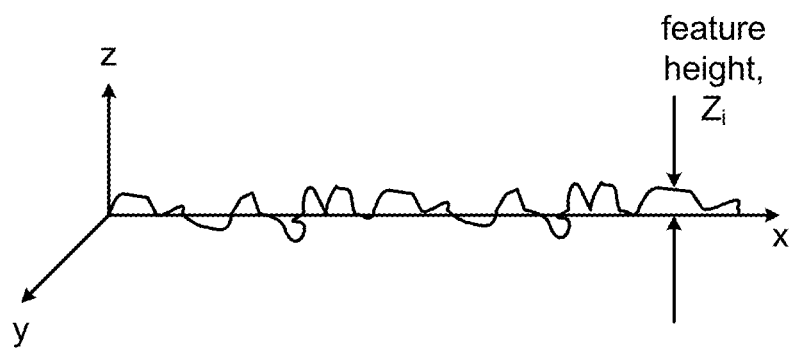
FIGS. 2A and 2B are schematic diagrams of dimensional parameters of surface features.
Figure 2B:
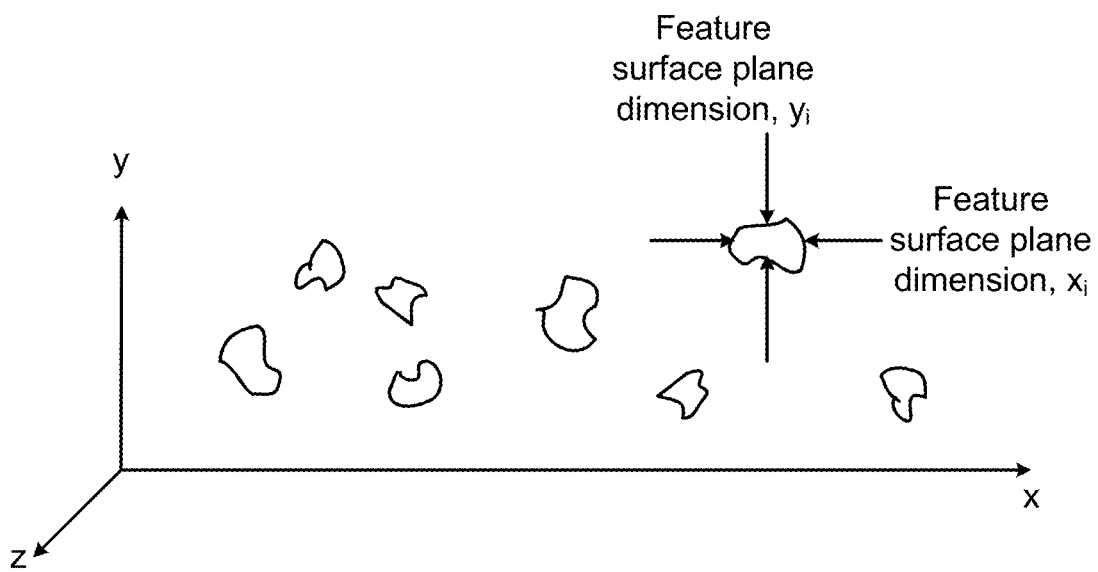

In addition to the anti-bacterial effects of the nano-scale surface morphology, the deposited nano-textured film may include antibacterial materials. For example, Ag is a biocompatible material that exhibits antibacterial properties. Furthermore, these antibacterial properties may not be reduced by incorporating Ag into another material to form an alloy (e.g., Ag doped titanium, Ag doped titanium dioxide). Low (e.g., <10%) Ag concentrations may be sufficient to provide antibacterial benefits. A zone of inhibition may indicate antibacterial properties of an antibacterial agent. Referring to FIG. 1, a schematic diagram of a zone of inhibition is shown. The zone of inhibition 110 is an area around an antibacterial agent, for example Ag 120, characterized by an absence of bacterial growth 130. A radius of the zone of inhibition 110 for anti-biotic medications may be ≤30 mm. The radius of the zone of inhibition 110 for Ag 120 may be ≤3 mm. Alternatively and/or additionally, Ag may prevent and/or reduce a rate of biofilm formation. For example, the biofilm formation may produce an inflammatory response in the host as a precursor to bacterial infections. Prevention and/or reduction of the biofilm formation may prevent and/or reduce the occurrence of the infections.

Elution of the Ag may affect the antibacterial properties of the deposited film. In an elution process, Ag+ions may be released from a solid surface in the presence of moisture and bind to cell membranes. Subsequently, Ag+ions may be absorbed by cells which may interrupt protein, DNA, and RNA functions within the bacteria cells. A rate of elution (e.g., $\mu g/cm^2$/unit time as determined by a Ringers solution) may depend on a processing method used to incorporate the Ag into the solid surface. For example, a low elution rate of 0.5-10 $\mu g/cm^2$/year of Ag may indicate the capacity for the deposited film that includes the Ag to provide protection antibacterial for periods of time on the order of 100 years. This elution rate may be too low to provide antibacterial protection to the surrounding tissue, however, it may be effective for controlling cell growth directly on the treated surface. For example, a relatively small zone of inhibition (e.g., <3 mm) may correspond to reduced antibacterial protection to tissue surrounding the deposited film while reducing or eliminating the formation of a biofilm on the deposited film. The biofilm may be the precursor to bacterial growth. A film deposition technique and/or process may determine a bulk and/or a surface density and a bulk and/or a surface morphology. In turn, the density and/or the morphology, particularly the surface density and surface morphology may determine the elution rate for components of the film.

One method of depositing the biocompatible antibacterial film with nano-scale features is physical vapor deposition in the presence of an accelerated ion beam, for example, but not limited to, ion beam assisted deposition (IBAD). During IBAD, a vapor flux of one or more atomic species is generated with an electron-beam evaporator. The one or more atomic species condense on the substrate to grow a deposited film. Concurrently, ions (for example, but not limited to, nitrogen (N), oxygen (O), and/or noble gases such as argon (Ar), neon (Ne), xenon (Xe), helium (He) etc.) are accelerated into the growing film. This concurrent ion bombardment affects properties of the deposited film including, for example, morphology, density, film stress, crystallinity, and chemical composition. For example, physical vapor deposition (PVD) without ion beam assistance typically produces a porous, columnar microstructure. In contrast, energy from the ion beam in IBAD may increase nucleation density and surface mobility of atoms in the vapor flux and thereby reduce or eliminate this porous, columnar microstructure.

Additionally, the ion beam may produce physical sputtering and re-deposition of atoms from the vapor flux that are loosely bound to the surface of the substrate and/or the surface of the growing film. These atoms may be forced into voids which may increase the film density as the film growth proceeds. The sputtering and re-deposition process may also create an intermixed zone of the substrate and coating atoms. Such an intermixed zone may improve film adhesion by eliminating and/or reducing the formation of interfacial voids. The ion beam may also enhance adhesion of the deposited film to the substrate by removing contaminant and/or oxide layers from the substrate surface before deposition of the film from the vapor flux. Removal of the contaminant and/or oxide layer increases atom reactivity between the substrate surface and the atoms of the vapor flux for improved bonding of the deposited film. Furthermore, the ion beam may break up crystal grains before they can grow to their natural size (e.g., their natural size being the crystal size in the absence of the ion beam bombardment). This process may yield a nano-crystalline microstructure, an amorphous microstructure, or a combination thereof. The deposition process parameters may allow control of the microstructure of the growing film. In this way, the microstructure may be tailored to particular applications.

Figure 3:
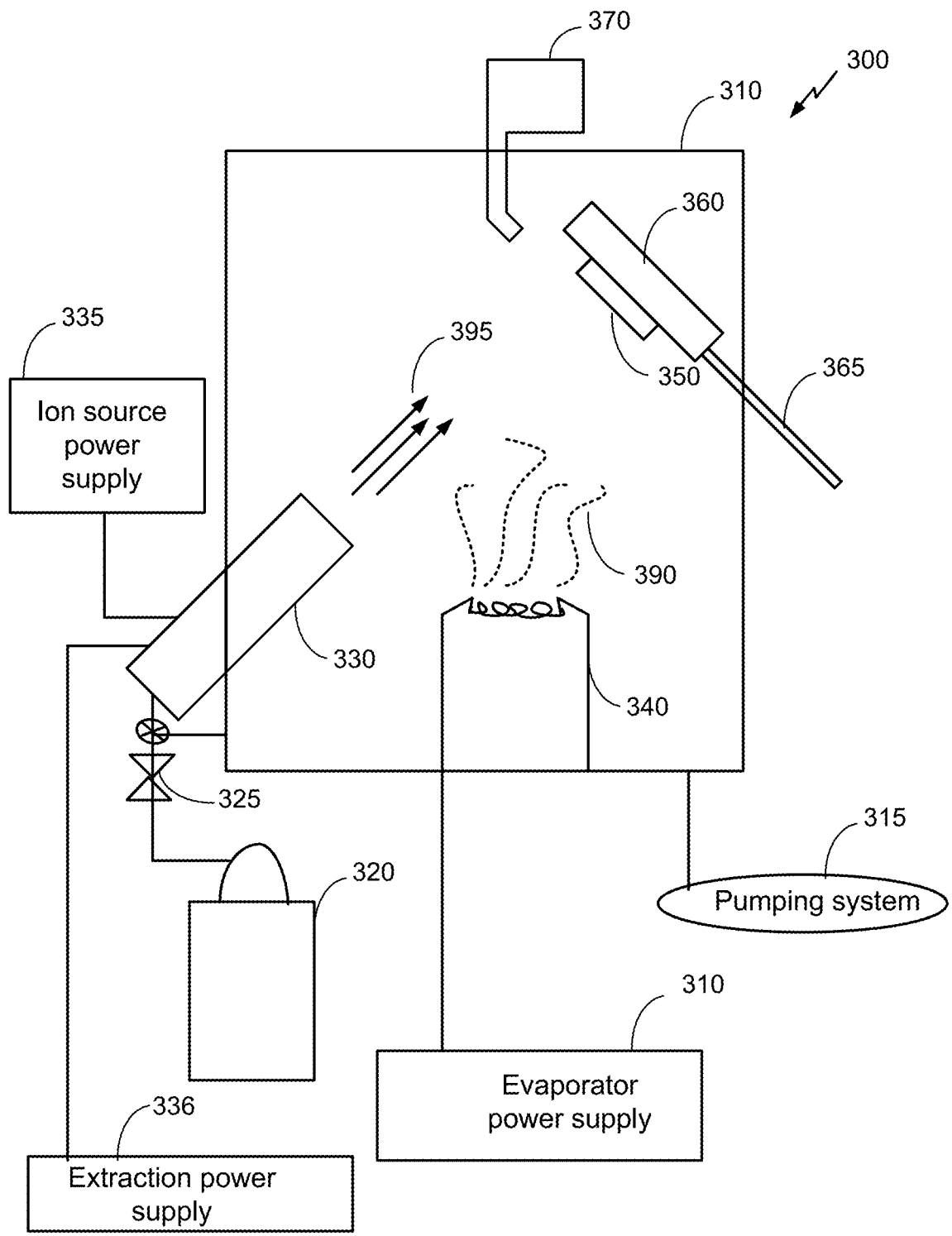
FIG. 3 is a schematic diagram of an example of a processing chamber for a physical vapor deposition (PVD) process.

Referring to FIG. 3, a schematic diagram of an example of a processing chamber for a physical vapor deposition (PVD) process is shown. The system 300 is an example and not limiting and may be altered, e.g., by having components added, removed, or rearranged. A quantity of each component in FIG. 3 is an example only and other quantities of each, or any, component could be used. Such systems are known in the art. The PVD process includes, for example but not limited to, an ion assisted PVD process such as ion beam assisted deposition (IBAD). For example, U.S. Pat. No. 5,236,509, herein incorporated by reference, describes an IBAD apparatus that is suitable for use in producing nano-textured antibacterial biocompatible films in accordance with the disclosure. The system 300 includes a processing chamber 310, a pumping system 315 and a gas supply source 320. The gas supply source 320 is coupled to a mass flow controller 325 and an ion source 330. The mass flow controller may provide gases to the processing chamber 310 at or below a flow rate of 100 standard cubic centimeters per minute (SCCM) flow rate. The gas supply source 320 is configured to supply one or more gases (e.g., Ar, Ne, Xe, He, O, N, etc.) to the ion source 330 and/or the processing chamber 310. The gas supply source 320 may be configured to supply the one or more gases as a backfill gas. The ion source may be a bucket type ion source or any other suitable ion source. A mass flow controller 325 regulates the rate of flow of the one or more gases from the gas supply source 320 to the ion source 330. An ion source power supply 335 maintains an arc discharge between the anode and the filaments and an extraction power supply 336 is configured to accelerate the ions through one or more accelerator grids of the ion source 330. The accelerated ions form an ion beam 395. The ion beam energy may be 50-5000 electron volts (eV). The extraction power supply 336 determines the ion beam energy and may determine the arrival rate of the ion beam. The ion source power supply and/or the mass flow controller may determine the arrival rate of the ion beam 395. The ion beam 395 may include one or more gas species.

An evaporator 340 also is mounted in the processing chamber 310 in operative association with the ion source 330. The evaporator 340 may be an electron beam evaporator. The evaporator 340 is designed to vaporize particular metallic evaporants (e.g., vapor plume 390) so as to dry-coat a specific substrate 350 therewith, being assisted in the dry-coating by an ion beam 395 emanating from the ion source 330. Metallic evaporants may include Ag, Ti, and their respective alloys, oxides and compounds. For example, Ti for evaporation may be 99.8% pure in 6 mm pellets, titania may be 99.9% pure, in 3-6 mm pellets, and Ag may be 3 mm pellets at 99.99% pure. The evaporator 340 may include one or more evaporant sources with each evaporant source configured to include one metallic evaporant. Further, the evaporator 340 may be configured to co-evaporate multiple materials and produce the vapor plume 390 including one or more materials. In this case, two or more materials may be co-deposited (i.e., deposited concurrently) onto the substrate 350. An electron beam current of the evaporator 340 determines a deposition rate for the metallic evaporants. The deposition rate of each of material may be independently controlled so that each species of multiple materials may have a respective deposition rate. In this way, one or more materials may be added to the vapor plume 390 and varying deposition rates of the various materials may be provided. During co-deposition, the ratio of the multiple materials in the vapor plume 390 may be the same through-out the deposition process or may change. For example, the vapor plume 390 may include more of a particular material than the other materials and the ratio between materials may be selected and controlled as a processing parameter.

The substrate 350 is provided in the processing chamber 310 with the aid of a suitable substrate holder 360. Preferably, the substrate holder 360 is mounted for both rotational and translational motion on a shaft 365. The substrate holder 360 may be a double-planetary fixture. This type of fixture rotates its components around two parallel axes, while simultaneously translating through the treatment zone. This may allow control of and optimization of packing density and coating uniformity for the deposited film. In an embodiment, the substrate holder 360 may be configured as a heat source or heat sink for the substrate. For example, the substrate holder may include a cooling system, such as a water cooling system. The system 300 may include a thickness monitor 370 in operative association with the substrate holder 360 to monitor the thickness of the film being deposited on the substrate 350 during operation of the system 300.

In general, the ion assisted PVD process includes a number of parameters, each of which can influence the properties of the film deposited on the substrate surface. Some of these parameters include evaporant deposition rate, electron beam current, arrival rate or current density of the ion beam, ion species, ion beam energy, backfill species, and backfill flow rate. Evaporant deposition rates can vary from about 0.5 Angstroms per second (Å/s) to approximately 100 Å/s. The electron beam current is controlled via a feedback loop with the thickness monitor 370 and adjusted based on the desired deposition rate. The arrival rate of the ion beam can be in a range between about 10 to about 500 microamperes per square centimeter per second ($\mu A/cm^2/sec$). The ion species may be one or more ionized noble gases, for example, Ar, Xe, Ne, He, etc. and/or one or more reactive gases, for example, O, N, etc. The ion beam energy may be 50 electron volts (eV) to about 1000 eV. The back fill species may be one or more reactive gases, for example, oxygen and/or nitrogen. The backfill flow rate may be ≤100 SCCM. Additionally, the crystal size (e.g., an average crystal size or a maximum crystal size) of the deposited film may be a function of the ion beam parameters.

Referring to FIG. 4, a method 400 of growing a biocompatible antibacterial film using PVD is shown. The method 400 is an example only and not limiting. The method 400 can be altered, e.g., by having stages added, removed, rearranged, combined, and/or performed concurrently. The biocompatible antibacterial deposited film may be an Ag doped Ti/TiO$_x$ film. A PVD processing chamber (e.g., the PVD system described above with regard to FIG. 3) may perform the method 400. In an example not limiting of the disclosure, the PVD processing chamber may be an ion beam assisted PVD (e.g., IBAD) processing chamber. Ion beam assisted physical vapor deposition may provide at least the advantage of generating the antibacterial deposited film with a nano-textured surface in a single processing equipment. In other words, deposition of this film may correspond to one step in a commercial or commercially scalable production process. The one step of this production process may include all of the stages of the method 400. FIGS. 5A, 5B, and 5C, as described below with regard to the stages of the method 400, are schematic diagrams of the deposition process and the biocompatible antibacterial film at the various stages of the method 400.

At stage 410, the method 400 includes providing a substrate in ion beam assisted physical vapor deposition processing chamber. For example, referring to FIGS. 3 and 5A, a substrate 510 may be mounted on the substrate holder 360 in the processing chamber 310. The substrate 510 may be a bio-implant, for example, but not limited to, a dental implant, a percutaneous device, an osseointegrated device, a percutaneous osseointegrated prosthesis, an orthopedic joint replacement, an orthopedic fixation pin, an orthopedic fixation plate, a percutaneous cochlear implant, a spinal disk replacement device, and/or a vascular device (e.g., a stent, a heart valve, etc.). At least a surface portion of the substrate 510 may be composed of Ti. In various implementations, the biocompatible substrate 510 may be composed at least in part of a thermoplastic, a stainless steel alloy, cobalt chromium, a ceramic (e.g., alumina, zirconia, aluminum oxynitride, titania, etc.), and/or combinations thereof.

At stage 420, the method 400 includes forming a deposited film by co-depositing a first material and a second material onto the substrate from a vapor plume, wherein at least the first material is biocompatible and at least the second material is antibacterial. For example, and with reference to FIGS. 3 and 5B, the stage 420 may include co-depositing a first material (e.g., Ti) and a second material (e.g., Ag) from a vapor plume onto the substrate 510 in the presence of an ion beam comprising noble gas ions. In this example, Ti may provide biocompatibility and Ag may provide biocompatibility along with antibacterial properties. In an implementation, the stage 420 may include selecting a ratio of the first material and the second material and forming the deposited film using the selected ratio. For example, the vapor plume may initially include one material (e.g., only Ti) and the second material (e.g., Ag) may be gradually added to the vapor plume such that an initial stage of deposition may be characterized by an increasing rate of deposition of the second material. The deposited material during the initial stage of deposition may form a transition layer (i.e., a gradual interface). The transition layer may have a varying composition across the thickness of the layer. In an embodiment, the transition layer may be approximately 500 Å thick. In another embodiment, the transition layer may be less than or equal to approximately 5000 Å thick. Gradually adding the second material into the vapor plume to produce this transition layer between the substrate and the deposited antibacterial layer and/or between the adhesion layer and the deposited antibacterial layer may provide improved adhesion properties compared to a deposited film without a transition layer (i.e., an abrupt change in constituent materials between the deposited film and the underlying layer or substrate). Subsequent to the initial stages, the deposition process may include a substantially constant rate of deposition of the second material. In this subsequent stage of deposition, the vapor plume may be 0.5%-100% of the second material. In an embodiment, at least a surface portion of the antibacterial layer may include elements of the first material and the second material (e.g., a mix of Ti and Ag). In an embodiment, at least a surface portion of the antibacterial layer may be substantially composed of the second material (e.g., approximately 100% Ag).

In an embodiment, the stage 420 may include backfilling the processing chamber with a reactive gas. The reactive gas may chemically react with the first material to form a ceramic. Co-depositing the ceramic with the second material may provide a ceramic matrix for the second material. The backfilling of the reactive gas may occur concurrently with the introduction of the second material or at any time during deposition of the first material or during co-deposition of the first material and the second material. The portion of the thickness of the deposited antibacterial layer that includes the ceramic matrix may depend on when the backfilling of the reactive gas occurs during the deposition of this layer. For example, a portion of the deposited antibacterial layer may not include the ceramic component and the ceramic component of the deposited antibacterial layer may be substantially confined to a surface layer of the antibacterial film.

As an example, and referring to FIG. 5C, the ceramic matrix may be a titania ($TiO_x$) matrix. The reactive gas may be oxygen 560 (e.g. $O_2$). The deposited antibacterial layer 570 may include Ag and titania and may be an Ag doped titania film. The $TiO_x$:Ag ratio of the film may vary based on deposition process parameters. The deposition rate of the $TiO_x$ may be 0.05-10 nm/sec. Backfilling with the oxygen 560 during Ti deposition may form the titania matrix. The flow rate of the oxygen 560 may be less than or equal to 100 SCCM. In an implementation, the oxygen ions may be added to the ion beam 395 in lieu of or in addition to backfilling with oxygen. The oxygen may be introduced prior to, concurrently with, and/or subsequently to the addition of Ag atoms 550 to the vapor plume 390. A longer exposure of the growing film to oxygen increases the amount of $TiO_x$ which may improves the durability of the deposited antibacterial layer.

In an embodiment, the stage 420 may include eliminating the first material from the vapor plume and adding a third material into the vapor plume in place of the first material and prior to addition of the antibacterial material. For example, the Ti deposition may be stopped and replaced by palladium deposition. The palladium deposition may form a palladium layer between the Ti adhesion layer and the Ag deposited antibacterial layer. The evaporant beam during the palladium deposition may be approximately 100% palladium and the vapor plume during the Ag deposition may be approximately 100% Ag.

In an embodiment, the stage 420 may include forming an adhesion layer between the substrate and the deposited film. The ion beam energy during the deposition of the adhesion layer may be 50-3000 eV and the ion beam arrival rate may be 10-500 $\mu A/cm^2$/sec. As shown in FIG. 5A, Ti atoms 520 may impinge upon and adhere to the substrate 510 in the presence of noble gas ions 530. The deposited Ti may form a Ti film 540. The Ti film 540 may provide an adhesion layer and may be 500 Å-0.5 µm thick. In an implementation, the adhesion layer may be a homo-metallic coating (e.g., a Ti film deposited on the Ti substrate is a homo-metallic coating). The deposition rate of the Ti may be 0.5-100 Å/second and the ion:evaporant atom arrival ratio, R, may be $0.02 \leq R \leq 1$. These deposition parameters may produce a smooth film surface (e.g., an RMS surface roughness of $R_q \leq 5$ nm). The ion beam may be a noble gas ion beam, for example an argon ion beam. By depositing the adhesion layer and the deposited antibacterial layer in one processing chamber, the adhesion layer may not be exposed to reactive gases outside of the processing chamber 310. Therefore an intervening oxide or other layer corresponding to a reaction between the adhesion layer material and the reactive gases outside of the processing chamber 310 may not form between the adhesion layer and the deposited antibacterial layer.

At stage 430, the method 400 includes nano-texturing the deposited film to produce nano-scale surface asperities that provides at least one of inhibition of bacterial growth, promotion of osseointegration, or promotion of epithelial attachment. During nano-texturing the ion beam energy may be 50-3000 eV. The ion beam arrival rate may be 10-500 $\mu A/cm^2$/sec. The ion:evaporant atom arrival ratio, R, may be $0.02 \leq R \leq 1$. The ion beam energy may produce nano-scale features or asperities due to sputtering rate. Referring further to FIG. 5C, the ions impinging upon the deposited antibacterial layer 570 may produce the nano-scale asperities 580 in the deposited antibacterial layer 570. The ion beam energy and ion beam arrival rate may be higher during nano-texturing than during the deposition of the adhesion layer.

In various implementations, the nano-texturing may occur before, during, and/or after backfilling the processing chamber 310 with the reactive gas. For example, increasing the ion beam energy during co-deposition of the Ti and the Ag may produce nano-textured features during growth of the deposited antibacterial layer 570. The ion beam energy required to produce nano-textured features in deposited Ti may be lower than that required to produce such features in deposited titania. The oxygen may be introduced subsequent to the forming of the nano-scale textural features (e.g., the asperities 580) in the deposited Ti and react with the deposited Ti to form titania throughout the thickness of the nano-scale features and/or in surface layers thereof.

The surface roughness of the deposited antibacterial layer may be greater than that of the adhesion layer. For example, the deposited antibacterial layer may have a surface roughness characterized by $R_q > 5$ nm. The ion beam energy and the ion beam current density during nano-texturing may provide a higher sputtering rate of the evaporant atoms than at lower ion beam energies and doses used to produce smooth film surface morphologies. As discussed above, the smooth surface is characterized by the relatively low roughness (e.g., $R_q < 5$ nm). The sputter yield, and therefore the texture of the deposited film, may be a function of the angle of ion beam incidence. For example, faces of features approximately normal to the ion beam are sputtered at a higher rate than faces of the features at angles to the ion beam and/or that are self-shielded by the features themselves. Over time the topography of the surface features becomes exaggerated, and a characteristic texture evolves. This characteristic texture may have a high roughness (e.g., $R_q > 5$ nm). Additionally, inclusions, grain defects, and other microstructural features of the film may determine the topography of the surface due to sputtering.

The ion beam assisted PVD process parameters may allow control of the nano-scale characteristics of the surface of the antibacterial layer. In this way, the nano-scale characteristics may be tailored to particular applications, including the inhibition of pathogenic bacterial growth, the promotion of fibronectin or other cellular adsorption, the promotion of osseointegration, the promotion of epithelial attachment, attraction of endothelial cells, and/or combinations thereof.

In an embodiment, the method 400 may be implemented with a combination of using PVD and/or ion beam assisted PVD for the stages 410 and 420 and using an anodization process for the nano-texturing. In such an embodiment, the method 400 may correspond to two or more steps in a commercial production process. Anodization may limit the types of substrates for the deposited film in terms of substrate composition. In contrast, ion beam assisted PVD is not restricted to anodizable substrates. Further, as the anodization requires removal of the substrate from the processing chamber, surface reactions may occur between the deposited film and reactive gases outside of the processing chamber. Such reactions may alter properties of the antibacterial film.

Referring to FIG. 6, with further references to FIGS. 1-5, a schematic diagram of an example of a titania/Ag antibacterial biocompatible film deposited on a Ti substrate is shown. The system 600 includes the substrate 610, the adhesion layer 615, and the deposited antibacterial layer 620. For example, the substrate 610 may be the bio-implant. The adhesion layer 615 may be a layer of deposited Ti. The thickness of the adhesion layer, $t_{adhesion}$, may be 100-1000 Å. In an embodiment, the adhesion layer 615 may be a homo-metallic layer. The homo-metallic characteristic of this film is produced because the atoms being deposited onto the substrate are atoms of the same element from which the substrate is substantially composed. The adhesion layer 615 may correspond to an intermixed zone. For example, the adhesion layer 615 includes Ti atoms from the vapor plume 390 along with Ti atoms from the substrate 610. As discussed above, the ion assisted PVD process may produce the intermixed zone in the adhesion layer 615 due to sputtering and re-deposition of Ti during ion beam assisted PVD of the Ti adhesion layer 615 on the Ti substrate 610. For the homo-metallic adhesion layer, there may be no interruption of metallic bonds. This may further enhances adhesion and durability of the adhesion layer 615 and the subsequent deposited antibacterial layer 620. The homo-metallic adhesion layer 615 may also reduce strain in the deposited film which may also enhance the adhesion of the deposited film 620. The homo-metallic adhesion layer 615 may additionally improve film adhesion by eliminating and/or reducing the formation of interfacial voids.

The deposited antibacterial layer 620 may be the nano-textured Ag doped Ti/TiO$_x$ film. The TiO$_x$ is the ceramic matrix of the deposited antibacterial layer 620. The ceramic matrix provides biocompatibility along with resistance to chemical and/or mechanical effects of the oral environment that may reduce the durability of the implant over time (i.e., reduce the longevity of the implant). Depending on when oxygen gas is introduced during the deposition process, the TiO$_x$ may be distributed throughout the entire thickness of the deposited antibacterial layer or may be substantially confined to a surface portion thereof. The thickness of the TiO$_x$ layer may depend on the thickness of the deposited antibacterial layer and may be a percentage thereof. For example, the TiO$_x$ may be a constituent of a surface layer of the deposited antibacterial layer while the bulk of the deposited antibacterial layer may be composed of Ti. The TiO$_x$ surface layer may be 100 Å-1000 Å thick or may be 100 Å-5 µm thick. The Ag is the antibacterial metallic component of the deposited antibacterial layer 620 and provides biocompatibility along with antibacterial properties. The atomic percentage of Ag in the deposited antibacterial layer 620 may be 0.5%-100%. In an embodiment, the atomic percentage of Ag in the deposited antibacterial layer 620 may be 0.5%-20%. A lower percentage of Ag provides antibacterial effects with less corrosion than a higher percentage of Ag. Further, incorporating the Ag into the deposited antibacterial layer 620 via the ion beam assisted PVD processing may result in a slow elution rate (e.g., 0.5-10 µg/cm$^2$/year) of Ag from the deposited antibacterial layer 620. This slow elution rate increases the longevity of the antibacterial efficacy of the deposited antibacterial layer 620. The film thickness, t, of the deposited antibacterial layer 620 may be 500 Å $\leq t_{antibacterial} \leq 10$ µm. A preferred film thickness may be 0.5-2 µm. The film thickness may vary by ±10-20% at various points on the substrate 610. The deposited antibacterial layer 620 may include 0-10% interstitial gas incorporated during the film growth. A surface of the film may include nano-scale asperities 630. These asperities may be produced by sputtering and re-deposition during the ion beam assisted PVD processing and/or by anodization processing. The RMS roughness, Rq, of the surface texture 630 may range from 5-100 nm.

The nano-scale asperities may substantially reduce and/or inhibit the growth of bacteria on the surface of the deposited film. Further, the dimensions of the nano-scale asperities may be tailored to the particular pathogenic bacteria of the biological environment of the implant. For example, the dimensions of the asperities may be based on mathematical modeling. Additionally, the nano-scale asperities may promote osseointegration, epithelial attachment, and/or endothelial attachment. For example, the asperities may attract bone cells, epithelial cells, and/or endothelial cells in the tissue at the bio-implant site and promote integration and/or attachment to the tissue at the bio-implant site.

In an embodiment, the deposited antibacterial layer may include Ag and palladium and may not include titania. In this case, the palladium may form a layer contiguous to the adhesion layer. The Ag may form a layer contiguous to the palladium and form the surface of the deposited antibacterial layer. In this case, the composition of the Ag layer may be approximately 100% Ag. The Ag layer may include the nano-texture asperities as introduced by sputtering in the ion beam assisted PVD processing.

In an implementation as a coating or surface of the dental implant, optimal properties of the antibacterial biocompatible film are those that minimize bacteria growth while maximizing osteoblast growth and promoting gingival fibroblast growth. However, promoting gingival fibroblast growth over that of bone growth would clinically lead to an unsupported implant. These properties may include surface morphology, film microstructure, film thickness, chemical/elemental content, adhesion, wettability, oxidation state, etc. For example, the antibacterial biocompatible film may demonstrate a reduction in colony forming periopathogenic bacteria on the order of $10^4$ (e.g., as measured in in vitro studies) as compared to a non-antibacterial film and/or a different antibacterial film (e.g., a film including antibiotics). Further, the film may demonstrate a statistically significant increase in osteoblast and gingival fibroblast activity over all controls while concurrently maintaining the aforementioned aggressive bacterial control. Additionally, $TiO_x$ may provide photocatalytic antibacterial properties. For example, the implant site in the oral cavity may be exposed to an ultraviolet (UV) light source. The $TiO_x$ may enhance the antibacterial effects of the UV light by promoting UV enhanced catalytic reactions that reduce and or minimize bacterial growth on the implant surface.

Referring to FIG. 7, with further reference to FIG. 6, an example of an atomic force microscopy (AFM) scan of the film in FIG. 6 is shown. The AFM image 700 shows a surface morphology characterized by nano-scaled features of approximately 10-1000 nm, as measured in the surface plane (e.g., the x and or y direction of FIG. 2B) and 10-1000 nm perpendicular to the surface plane (e.g., the z direction of FIG. 2A). The RMS roughness Rq for the film shown in FIG. 7 is 18.9 nm. Deposited film parameters and/or ion beam parameters may effect or determine the size and shape of these features. For example, as the deposited film thickness increases the features may be taller and may form pyramidal structures. A thinner coating may exhibit or produce shorter and more rounded features. As a further example, increasing the ion:evaporant atom arrival ratio produces sharper and/or thinner features for the same height. Such features may also be produced by a post deposition sputtering process. Decreasing the ion:evaporant atom arrival ratio may produce broader features for the same height.

In addition to AFM, scanning electron microscopy (SEM) may provide surface morphology and/or composition information. Deposited films may be further characterized by Rutherford Backscatter Spectroscopy (RBS) to determine a Ti:Ag ratio. Also water contact angles may be measured by the sessile-drop method (EasyDrop®, KRUSS®) to quantify surface wettability and surface energy. Coating adhesion testing with a standard tape-adhesion test (ASTM method D3359) may measure the adhesion of the coating on the substrate. Briefly, a pressure-sensitive tape (3M®) will be applied against the surface for approximately 90 seconds and then peeled off according to the guidelines by ASTM. X-ray photoelectron spectroscopy (XPS) may quantify oxidation state and/or a quantity of elements in or on the substrate and/or the deposited film.

Referring to FIG. 8, a schematic diagram of a dental implant system is shown. The system 800 is an example and not limiting and may be altered, e.g., by having components added, removed, or rearranged. A quantity of each component in FIG. 8 is an example only and other quantities of each, or any, component could be used. Dental implant 840 is designed for insertion into the mandible or jawbone 806 of a patient to support the mounting of a prosthesis. One or more natural teeth 805a and 805b may abut or border the implant site. Generally, a hole 850 is formed in the mandible or jawbone 806 of the patient, and the dental implant 840 is disposed in the hole 850 and allowed to undergo osseointegration. The hole 850 may be a cylindrical hole. The cross-sectional shapes of the hole 850 and the dental implant 840 as shown in FIG. 8 are examples only and not limiting. Other shapes are within the scope of the disclosure.

The dental implant 840, for example, a threaded dental implant, may have generally cylindrical body with an unthreaded, annular portion 845 at its proximal end. The remaining external surface of the generally cylindrical body may be substantially threaded. The threads 847 may allow the dental implant 840 to be turned into the cylindrical hole 850 formed in the jawbone 806 of the patient. The threads 847 may secure the dental implant and promote osseointegration. The threaded implant is an example only and not limiting of the disclosure. The prosthetic tooth 820 may be coupled to an abutment 830 which inserts into the dental implant 840.

Once implanted, various aspects of the oral environment may affect properties of the deposited film which may affect the longevity of the deposited film. For example, the chemical and/or biological environment in the mouth may affect film adhesion. As a further example, corrosion may change the nanostructure of the surface of the film.

Referring to FIG. 9, with further reference to FIGS. 1-8, a dental implant that includes an biocompatible antibacterial film is shown. The dental implant 840 includes a nano-textured biocompatible antibacterial film 920 on a substrate 910. The thickness of the film 920 may vary by 10%-20% on the non-planar surface of the substrate. The nano-scale surface texture of the film 920 promotes osseointegration (e.g., osseointegration in the first days, weeks and/or months after implant) together with long term antibacterial activity (e.g., antibacterial activity in the weeks, months, and/or years after implant). For example, the antibacterial activity of the film may exceed 90 days or may exceed 1 year or may exceed 10 years. The osseointegration is integration of the implant and surrounding bone tissue. In an embodiment, the crown (e.g., the prosthetic tooth 820) may include the biocompatible antibacterial film.

Referring to FIG. 10, an example of a percutaneous osseointegrated prosthetic system (PODS) that includes an antibacterial biocompatible film is shown. The PODS includes a bone implant region 1010, a subcutaneous collar 1020, a percutaneous post 1030, an exoprosthetic 1040, and an antibacterial biocompatible film 1050. The region of the PODS that includes the film 1050 in FIG. 10 is an example only and more or less of the PODS may include the antibacterial biocompatible film. The thickness of the film 1050 may vary and the film 1050 may or may not be continuous along the surface of the PODS. A PODS implant that includes the antibacterial biocompatible film of FIG. 6 with film properties tailored to minimize bacterial growth and maximize epithelial cell integration may provide benefits with regard to prevention and/or reductions of infection in PODS applications. The nano-textured titania/Ag film may reduce adherence of pathogens including Staphylococcus aureus, Pseudomonas aeruginosa, and epidermidis. Additionally, such a film may promote adhesion of fibroblast cells and keratinocyte cells. An epithelial marsupialization assessment may indicate the epithelial marsupialization rate and the periprosthetic tissue response to the film surface.

Other Considerations

The methods, systems, and devices discussed above are examples and other embodiments are within the scope of the invention. Various alternative configurations may omit, substitute, or add various procedures or components as appropriate. Configurations may be described as a process which is depicted as a flow diagram or block diagram. Although each may describe the operations as a sequential process, many of the operations can be performed in parallel or concurrently. In addition, the order of the operations may be rearranged. A process may have additional stages not included in the figure.

Specific details are given in the description to provide a thorough understanding of example configurations (including implementations). However, configurations may be practiced without these specific details. For example, well-known processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional stages or functions not included in the figure.

Having described several example configurations, various modifications, alternative constructions, and equivalents may be used without departing from the disclosure. For example, the above elements may be components of a larger system, wherein other rules may take precedence over or otherwise modify the application of the invention. Also, a number of operations may be undertaken before, during, or after the above elements are considered. Also, technology evolves and, thus, many of the elements are examples and do not bound the scope of the disclosure or claims. Accordingly, the above description does not bound the scope of the claims. Further, more than one invention may be disclosed.

As used herein, including in the claims, "or" as used in a list of items prefaced by "at least one of" or "one or more of" indicates a disjunctive list such that, for example, a list of "at least one of A, B, or C" means A or B or C or AB or AC or BC or ABC (i.e., A and B and C), or combinations with more than one feature (e.g., AA, AAB, ABBC, etc.). Also, as used herein, unless otherwise stated, a statement that a function or operation is "based on" an item or condition means that the function or operation is based on the stated item or condition and may be based on one or more items and/or conditions in addition to the stated item or condition. As used herein, including in the claims, unless otherwise stated, a statement that a function or operation is "based on" an item or condition means that the function or operation is based on the stated item or condition and may be based on one or more items and/or conditions in addition to the stated item or condition.

What is claimed is:

1. A method of depositing a biocompatible antibacterial film using ion beam assisted deposition (IBAD) comprising:
   providing a substrate in a IBAD processing chamber;
   forming a deposited film by co-depositing a first material and a second material onto the substrate from a vapor plume, wherein the vapor plume initially includes the first material and the second material is added to the vapor plume such that forming the deposited film is characterized by an initial layer comprising the first material and a second layer comprising a combination of the first and the second materials, wherein at least the first material is biocompatible and at least the second material is antibacterial; and
   simultaneously nano-texturing the deposited film through at least a portion of its thickness to produce nano-scale surface asperities by concurrent bombardment with an ion beam having an energy of 50 eV-3000 eV, and a roughness of the nano-texture of the deposited film is in a range from 5-1000 nanometers.

2. The method of claim 1 wherein the nano-texturing the deposited film provides for at least one of inhibition of bacterial growth, promotion of osseointegration, promotion of epithelial attachment, or promotion of endothelial attachment.

3. The method of claim 1 further comprising forming the deposited film and nano-texturing the deposited film in the presence of an ion:evaporant atom arrival ratio, R, of $0.02 \leq R \leq 1$.

4. The method of claim 1 further comprising:
   backfilling the processing chamber with a reactive gas; and
   forming the deposited film in the presence of the reactive gas such that the deposited film includes a ceramic component, the ceramic component being composed of the first material and an element of the reactive gas.

5. The method of claim 1 comprising:
   selecting a ratio of the first material and the second material; and
   forming the deposited film by co-depositing the first material and the second material using the selected ratio.

6. The method of claim 1 wherein the substrate comprises one or more of a dental implant, a percutaneous device, an osseointegrated device, a percutaneous osseointegrated prosthesis, an orthopedic joint replacement, an orthopedic fixation pin, an orthopedic fixation plate, a percutaneous cochlear implant, a spinal disk replacement device, or a vascular device.

7. The method of claim 1 wherein the initial layer is less than or equal to 5000 angstroms thick.

8. The method of claim 1 wherein the initial layer is approximately 500 angstroms thick.

9. The method of claim 1 wherein the second material is gradually added to the vapor plume at an increasing rate.

10. The method of claim 9 wherein forming the deposited film includes a subsequent third layer following the second layer, wherein the vapor plume is substantially composed of the second material.

\* \* \* \* \*